United States Patent [19]

Porath

[11] Patent Number: 4,696,980
[45] Date of Patent: Sep. 29, 1987

[54] SULFONE ACTIVATED THIOETHER ADSORBENTS FOR THE SEPARATION OF PROTEINS AND THE LIKE

[76] Inventor: Jerker Porath, Bodalsvägen 4A, S-18136 Lidingö, Sweden

[21] Appl. No.: 729,344

[22] Filed: Apr. 30, 1985

[30] Foreign Application Priority Data

May 17, 1984 [SE] Sweden .................................. 8402663

[51] Int. Cl.$^4$ .......................... C08C 8/00; C07H 5/00
[52] U.S. Cl. .............................. 525/326.1; 525/329.4; 525/330.3; 525/330.4; 525/330.5; 536/1.1; 536/18.7; 536/54; 536/55.1; 536/122; 536/123; 530/415; 530/812; 530/815; 530/816; 435/181; 435/178; 435/814; 435/815; 436/528; 436/529; 436/531; 436/532
[58] Field of Search ............... 536/123, 122, 1.1, 18.7, 536/54, 55.1; 530/415, 412, 815, 812; 435/180–181; 436/531–532; 525/326.1, 329.4, 330.3, 330.4, 330.5

[56] References Cited

U.S. PATENT DOCUMENTS

| | | | |
|---|---|---|---|
| 3,085,072 | 4/1963 | Zima et al. | 525/330.4 |
| 3,396,198 | 8/1968 | Welch | 568/32 |
| 3,517,068 | 6/1970 | Perrino | 568/32 |
| 3,642,908 | 3/1972 | Burness | 568/32 |
| 3,748,364 | 7/1973 | Tesoro | 568/32 |
| 3,875,084 | 4/1985 | Weil | 525/330.4 |
| 4,374,061 | 2/1983 | Bing | 260/112 R |

FOREIGN PATENT DOCUMENTS

0055235  6/1982  European Pat. Off.
 361320  5/1973  Sweden.

OTHER PUBLICATIONS

Avrameas et al, C.A., vol. 72, 1970, #63566w.
Methods of Enzymology, vol. 34, ed. Jakoby et al, 1974, pp. 24–27.
"Synthesis of polysulfone-Sulfides by Polyadditions of Dithiols to Divinyl Sulfones", *Journal of Polymer Science;* Polymer Chemistry Edition, vol. 19, 583 590; 1981.
"Aliphatic Compounds", *Chemical Abstracts,* vol. 68, p. 5703, No. 59110, (1968).

*Primary Examiner*—John Kight
*Assistant Examiner*—Garnette D. Draper
*Attorney, Agent, or Firm*—Young & Thompson

[57] ABSTRACT

The adsorbent consists of a solid phase, completely or partially penetrated by or surface-coated with a hydrophilic molecular polymer netting to which has been bound substituents or cross bridges having chain sequences of the structure $$X-CH_2-CH_2-SO_2-CH_2-CH_2-S-Y$$

where X is ether oxygen, a thioether sulfur atom or a nitrogen atom and Y is a substituted or unsubstituted alkyl, aryl or heteroaromatic group. The solid phase consists of particles with a diameter of less than 1 mm and the molecular polymer netting consisting of a cross-linked polyhydroxy polymer such as a polysaccharide, preferably a polygalactane such as agar or agarose or a cross-linked polyamide, e.g. polyacryl amide. Y can be hydroxy alkyl or mercapto alkyl, or phenyl alkyl or phenyl substituted with halogen or nitro groups. The adsorbent is prepared by first converting in a known manner a hydrophilic polymer containing OH and/or CONH$_2$ groups to a vinylsulfone substituted polymer for subsequent contact in alkali solution, with or without organic solvent, with an organic thiol compound. The adsorbent can be used for the fractionation of biopolymers such as nucleic acids, nucleotides, proteins and polypeptides, and has been found particularly well suited for the fractionation of serum proteins.

4 Claims, No Drawings

SULFONE ACTIVATED THIOETHER ADSORBENTS FOR THE SEPARATION OF PROTEINS AND THE LIKE

Adsorbents of different types are used within the fields of biochemistry and biotechnology for the isolation of macro- as well as "micromolecules" and for the immobilization of e.g. enzymes for technical applications, as well as antigens and antibodies for the diagnosis of diseases. The invention relates to this category of adsorbents although distinguished from conventional types of adsorbents with respect to certain characteristic features.

The inventive object is a finely divided absorbent consisting of particles which in an especially useful form are spherically shaped with a diameter on the order of 1–1000 $\mu$m. The particles have a polymeric netting penetratrating the particles entirely or coating the surface thereof and containing substituents or cross links with a characteristic atomic sequence in the form of a chain having a sulfone group separated from a thioether sulfur via an ethylene bridge: X—$SO_2$—$CH_2$—$CH_2$—S—Y. Thioether S is furthermore flanked by a group Y which can terminate a chain being ether-bound at the other end by X with two or more carbon atoms to the polymeric netting. Groups Y and X can also be linked together with different branches of the netting so that the group —$SO_2$—$CH_2$—$CH_2$—S— forms a cross-linking bridge between two polymer chains in the netting.

X is selected from the group consisting of ether oxygen, thioether sulfur, and nitrogen. Y is selected from the group consisting of a heteroaromatic ring having at least one nitrogen atom, a phenyl group substituted with at least one nitro group, and a phenyl group substituted with at least one nitro group, and further substituted with alkyl, acyl, amino, or hydroxy groups.

The characterizing feature of the inventive object is its adsorption properties, the nature of which can be similar to that of so-called hydrophobic adsorbents. For example, the adsorption of proteins is increased in the presence of high concentrations of aqueous-structure organized salts such as alkali chlorides, alkali sulfates and magnesium sulfates, for example. It is apparent however that adsorbents according to the invention preferably adsorb other proteins than is the case with hydrophobic adsorbents based on the presence of alkyl groups containing e.g. 8–18 carbon atoms. What is unexpected however is that Y can be terminated by a hydroxyl group making in this way the whole structure relatively hydrophilic. Consequently, the group —$SO_2$—$CH_2$—$CH_2$—S—$CH_2$—$CH_2$—OH for example yields an excellent adsorption agent for certain serum proteins (which are not easily adsorbed on hydrophobic alkylized gels). The adsorption affinity of the group can be weakened or strengthened depending on the nature of X. The adsorption affinity will be stronger if the characteristic sequence is doubled:

—$SO_2$—$CH_2$—$CH_2$—S—$CH_2$—$CH_2$—$SO_2$—$CH_2$—$CH_2$—S—$CH_2$—$CH_2OH$.

The adsorption character will change if an ionogenic group is introduced, for example —$SO_2$—$CO_2$—$CH_2$—S—$CH_2$—$CH_2$—COOH.

Even such modified adsorbents are valuable complements to the abundance of separation products used at present within the field of protein and nucleic acid chromatography.

As additional examples of groups Y according to the invention can be mentioned substituted aromatics and heterocyclic ligands. Some of these are stated in the exemplary embodiments. Of special interest are the strongly hydrophobic Y groups, for example $C_nH_{2n+1}$, where $n \geq 6$. The combined effect of the hydrophobic interaction and the —S— dependent adsorption reinforced by —$SO_2$— can be utilized for protein immobilization.

It is evident from the aforegoing that one embodiment of the invention can consist of particles having a netting for proteins which is permeable all the way to the center. In accordance with a second alternative, only the surface of the particle is covered with netting that is permeable for proteins, and the particle nucleus will therefore not include the group that is characteristic for adsorption. A third alternative may consist of a more or less heavy layer of netting surrounding an impermeable nucleus. The nucleus in this case can be arbitrarily formed and may constitute for example a fiber, the inner surface of a hose, a beaker or any other vessel, etc.

For the permeation of macromolecules and in order to clearly disclose the characteristic adsorption properties, the polymeric netting must be of a specific nature; it must be hydrophilic and permeable for the macromolecules, it must be resistent within a pH range where proteins can be adsorbed without being damaged, preferably within the range of pH 4–8 but also within a wider pH range. The chemical properties of the polymeric netting must further be well adpated for the introduction of the group which is characteristic for the adsorption. With regard to the polymeric netting, the invention is restricted by said limitations to hydrophilic polymers of the following types: polyalcohols, for example polyvinyl alcohol, polyhydroxy methanes, polysaccharides, crosslinked hexitholes and polyamides such as cross-linked polyacryl amide. Cross-linked polyamines and polyacides can also be mentioned; it should be noted however that the adsorption will be more complicated by the presence of the inogenic groups. The gel netting can also consist of silica gel substituted with hydrophilic groups such as glycerol substituents, or groups such as $$-O-\underset{\underset{CH_3}{|}}{\overset{\overset{CH_3}{|}}{Si}}-CH_2-CH_2-CH_2-NH-$$

An especially useful adsorbent according to the invention is cross-linked agar. Insertion of the adsorbing group may to advantage take place by reacting the polymer matrix with divinyl sulfone for subsequent conversion of the thus cross-linked and simultaneously activated product with a mercaptan, for example mercapto ethanol:

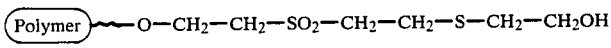

or cysteine

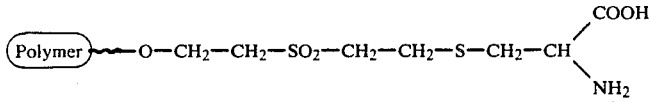

or thiophenol

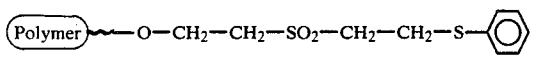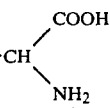

or a thio substituted heterocyclic compound, for example 6-thioadenine

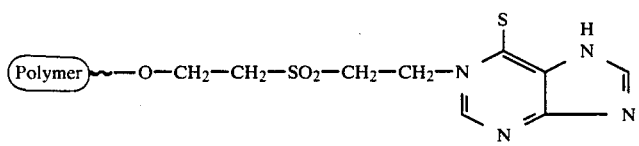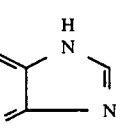

The divinyl sulfone activated matrix can also be allowed to react with dithiol, for example

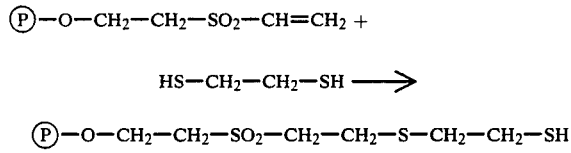

where (P) represents the polymer matrix, which can be made to react with additional DVS, obtaining in this way a new type of cross-link:

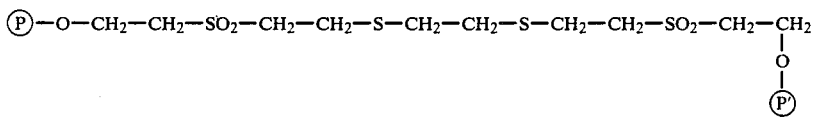

It is also possible to desaturate the matrix, activated for the second time, with mercapto ethanol for example:

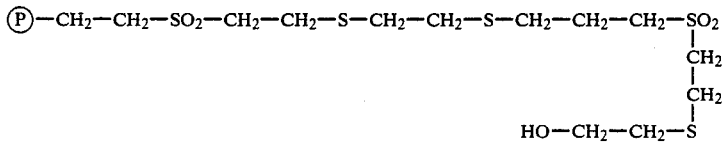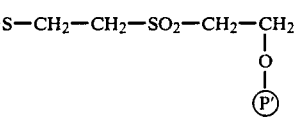

All the above-mentioned varieties of substituted polymer nettings will yield adsorbents according to the invention.

EXAMPLE 1

Particulate agarose gel is washed in a Büchner funnel with de-ionized water. The gel is sucked free from intermediate solution and a gram of gel is weighed and suspended in a ml 0.5 ml of $Na_2CO_3$ solution in a round flask. 0.1 a ml of divinyl sulfone is added and the mixture is allowed to react overnight at room temperature under agitation. The activated gel obtained in this way is transferred to a Büchner funnel and washed with deionized water.

The activated gel is moved to a reaction vessel while adding a ml of 0.1M $NaHCO_3$ solution and 0.1 a ml mercapto ethanol. After a contact period of 15 hours, the gel is transferred to a Büchner funnel and washed with deionized water.

The gel was tested with regard to its ability of adsorbing proteins: a chromatographic bed was packed with the gel in 0.1M Tris-CHl buffer at pH 7.6 containing 0.5M $K_2SO_4$. Various amounts of human serum were separated in different chromotographic trials in the gel bed. Upon introduction of 90 absorbence units (280 nm) into the bed, 35 units were adsorbed of which 26 were desorbed after washing the bed with buffer without potassium sulfate. The remainder was desorbed with 30% isopropanol included in the buffer.

In a second trial, 1300 absorbence units of dialyzed human serum were fed in. 180 units were adsorbed of which 240 were desorbed upon washing with sulfate-free buffer.

Thus 39% and 23%, respectively, of the serum proteins were adsorbed. A gel electrophoretic analysis disclosed that immunoglubulines constituted the main component of the adsorbence, and that nothing or only a slight amount of the serum albumine was adsorbed to mercapto ethanol-bound divinyl sulfone activated agar gel.

EXAMPLE 2

An assay was carried out according to Example 1 with the difference that cellulose powder was used instead of agarose particles, and that the percentage of divinyl sulfone was raised to 20% upon activation.

The adsorption test indicated that the capacity for serum protein was approx. 30% of the corresponding amount of agarose gel.

EXAMPLE 3

An assay was carried out with epichlorohydrin-treated polyacryl amide (commercially available Eupergite C). The oxirane gel was converted to SH gel with NaSH in 0.1M NaHCO$_3$ at pH 9 overnight and was then treated as the agar gel in Example 1.

The polyacryl amide derivative appeared to have the capacity of about half that of the agarose derivative per milliliter of gel bed.

EXAMPLE 4

An assay was carried out in the same way as in Example 1 but with the difference that the mercapto ethanol was replaced by ethanol amine. Adsorption tests disclosed that only minor amounts of serum protein were adsorbed, and that no proteins were desorbed either in sulfate-free buffer or with isopropanol included in the buffer.

EXAMPLE 5

The same procedure as in Example 1 was employed but using 0.1 a glycine instead of 0.1 ml mercapto ethanol. All the protein from one serum test passed a gel bed prepared as in Example 1.

EXAMPLE 6

An assay was carried out as in Example 1 but with the use of 2.3-dimercapto ethanol instead of mercapto ethanol. The adsorption test disclosed that upon introduction of 100 adsorption units of serum protein in the column, 32 units were adsorbed of which 15 were eluated by excluding K$_2$SO$_4$ from the buffer.

I claim:

1. Adsorbent for separation and immobilization, comprising a hydrophilic polymeric netting selected from the group consisting of agar, agarose, cellulose, polyacrylamide and polyvinyl alcohol, said netting comprising cross-links bound to said netting, said cross-links having the structure

where Y is selected from the group consisting of a heteroaromatic ring having at least one nitrogen atom, a phenyl group substituted with at least one nitro group, and a phenyl group substituted with at least one nitro group, and further substituted with alkyl, acyl, amino, or hydroxy groups; and X is selected from the group consisting of ether oxygen, thioether sulfur, and nitrogen.

2. Adsorbent according to claim 1, and particles of diameter less than 1 mm, to which said particles said adsorbent is surface-coated.

3. Adsorbent according to claim 2, wherein said particles are porous and said adsorbent penetrates into said particles.

4. Adsorbent according to claim 1, wherein said polyhydroxy polymer is selected from the group consisting of agar and agarose.

* * * * *